(12) United States Patent
Nilsson et al.

(10) Patent No.: US 8,302,731 B2
(45) Date of Patent: Nov. 6, 2012

(54) HEARING PROTECTOR

(75) Inventors: Sigvard Nilsson, Vamamo (SE); Henrik Nordin, Forsheda (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/203,253

(22) PCT Filed: Mar. 5, 2010

(86) PCT No.: PCT/US2010/026348
§ 371 (c)(1),
(2), (4) Date: Aug. 25, 2011

(87) PCT Pub. No.: WO2010/111013
PCT Pub. Date: Sep. 30, 2010

(65) Prior Publication Data
US 2012/0012418 A1 Jan. 19, 2012

(30) Foreign Application Priority Data
Mar. 27, 2009 (EP) ..................................... 09156541

(51) Int. Cl.
*H04R 25/00* (2006.01)
(52) U.S. Cl. ............ 181/129; 181/130; 181/135; 2/209; 2/423

(58) Field of Classification Search ................... 181/129, 181/130, 135; 2/209, 423
See application file for complete search history.

(56) References Cited

U.S. PATENT DOCUMENTS

| | | | | | |
|---|---|---|---|---|---|
| 3,506,980 | A | * | 4/1970 | Jackson | 2/209 |
| 3,944,018 | A | * | 3/1976 | Satory | 181/175 |
| 4,572,324 | A | * | 2/1986 | Fidi et al. | 181/129 |
| 4,958,697 | A | * | 9/1990 | Moody | 181/129 |
| 5,920,911 | A | * | 7/1999 | Cushman | 2/209 |
| 6,412,593 | B1 | * | 7/2002 | Jones | 181/129 |
| 6,820,717 | B2 | * | 11/2004 | Fleming et al. | 181/135 |
| 7,305,992 | B2 | * | 12/2007 | Fleming | 128/864 |
| 2008/0128198 | A1 | * | 6/2008 | Du et al. | 181/129 |

FOREIGN PATENT DOCUMENTS
DE 1512666 A1 6/1969
GB 1144295 3/1969
* cited by examiner

*Primary Examiner* — Forrest M Phillips

(57) ABSTRACT

The present invention provides a hearing protector comprising two ear cups which are designed to cover the ears of the wearer of the hearing protector, and sealing rings (2) which are secured along the peripheries of the ear cups, the sealing rings each displaying at least one circumferential lamella (5, 6, 7), being manufactured from a resilient, possibly elastic material, and being formed to sealingly abut, around the wearer's ears, against the wearer's head, wherein the lamella (5,6, 7), at least along its edge regions located most proximal the wearer's head, display portions (13, 14, 15) which, in a direction towards the wearer, are arched from a central region (3) in the sealing ring (2) out towards its periphery (1).

13 Claims, 2 Drawing Sheets

HEARING PROTECTOR

CROSS REFERENCE TO RELATED APPLICATIONS

This application is a national stage filing under 35 U.S.C. 371 of PCT/US2010/026348, filed Mar. 5, 2010, which claims priority to European Application No. 09156541.6, filed Mar. 27, 2009, the disclosure of which is incorporated by reference in its/their entirety herein.

TECHNICAL FIELD

The present invention relates to a hearing protector comprising two ear cups which are designed to cover the ears of the wearer of the hearing protector, and sealing rings which are secured along the peripheries of the ear cups, the sealing rings each displaying at least one circumferential lamella being manufactured from a resilient, possibly elastic material, and being formed to sealingly abut, around the wearer's ears, against the wearer's head.

BACKGROUND

Hearing protectors of the type which have two ear cups which are intended to enclose and seal about the ears of a wearer are previously known in a plurality of different variations. In order to ensure the sealing between the ear cup and the head of the wearer, the ear cup has, along its periphery, a sealing ring which is formable, possibly elastic, and which establishes a sealing abutment against the wearer's head, surrounding the wearer's ears. Normally, the sealing ring is manufactured from a foamed material, which is housed in a foil-like casing, which is that part of the sealing ring abutting against the head of the wearer.

By adapting the properties of the foamed material, optimization of the sealing ring may be made, both as regards sound damping, sealing and the feeling of more or less comfort in wearing the hearing protector. Thus, it has proved that a more rigid and hard sealing ring increases the sound damping properties of the hearing protector, but reduces the level of comfort for the wearer of the hearing protector. In addition, an excessively hard sealing ring can also jeopardize the sealing action between the sealing ring and the wearer's head, since an overly hard sealing ring is incapable of forming itself in adaptation to the head of the wearer to a sufficient degree.

As regards the perceived comfort when wearing a hearing protector, the ambient temperature is a major factor, since perspiration often occurs both interiorly in the hearing protector and between the sealing ring of the hearing protector and the skin or the wearer. Hence, excessive perspiration is perceived as unpleasant.

Another aspect concerning perspiration is that the hearing protector becomes dirty, and so should be cleaned at regular intervals, which is difficult or even impossible when foamed material is used in the sealing ring.

A further aspect in storage or use of hearing protectors at high ambient temperatures, for example if a hearing protector is left in a motor car or an airplane out in the sunlight, is that the high temperatures that prevail can considerably affect the material properties in the foamed material which is normally used in the sealing rings. A hearing protector heated in this manner can have completely different properties than those which were originally intended.

Other problems may occur in severe cold, where many foamed materials show a tendency to become excessively hard.

Hearing protectors are previously known in the art which display sealing rings of another type than the type under consideration here. Thus, U.S. Pat. No. 5,920,911 discloses a hearing protector where the above-considered sealing ring consisting of a foamed material has been replaced by a sealing ring that comprises a number of circumferential lamellae (designated lips) disposed in a radial direction with interspacing outside one another. These lamellae are produced from a resilient, possibly elastic material and have edge surfaces which are intended, under deformation, to sealingly abut against the wearer's head around the wearer's ear. These lamellae have attenuated edge portions facing towards the wearer's head, these portions constituting the actual contact surfaces against the wearer's skin. Such contact surfaces afford more or less only straight line contact against the skin, for which reason the abutment pressure may be considerable, with great risk that the hearing protector is perceived as uncomfortable already after only a short period of use.

In certain embodiments, there are disposed between the lamellae porous damping bodies produced from fibrous or foamed material, which would render an efficient cleaning of a hearing protector formed in this manner more or less impossible.

The present invention has for its object to design the hearing protector intimated by way of introduction such that the drawbacks inherent in the prior art technology are obviated. In particular, the present invention has for its object to realize a hearing protector where the sealing ring offers a high degree of comfort, combined with effective sealing and good sound damping. Further, the present invention has for its object to design the hearing protector according to the present invention such that a choice of materials is possible, which entails resistance also to greatly elevated temperatures. Finally, the present invention has for its object to realize a hearing protector where the sealing ring may be produced in a simple and economical manner and where it may simply be kept clean.

The objects forming the basis of the present invention will be attained if the hearing protector intimated by way of introduction is characterized in that the lamella, at least along its edge regions located most proximal the wearer's head, display portions which, in a direction towards the wearer, are arched from a central region in the sealing ring out towards its periphery.

BRIEF DESCRIPTION OF DRAWINGS

The present invention will now be described in greater detail hereinbelow, with reference to the accompanying Drawings. In the accompanying Drawings.

DETAILED DESCRIPTION

Figure 1:
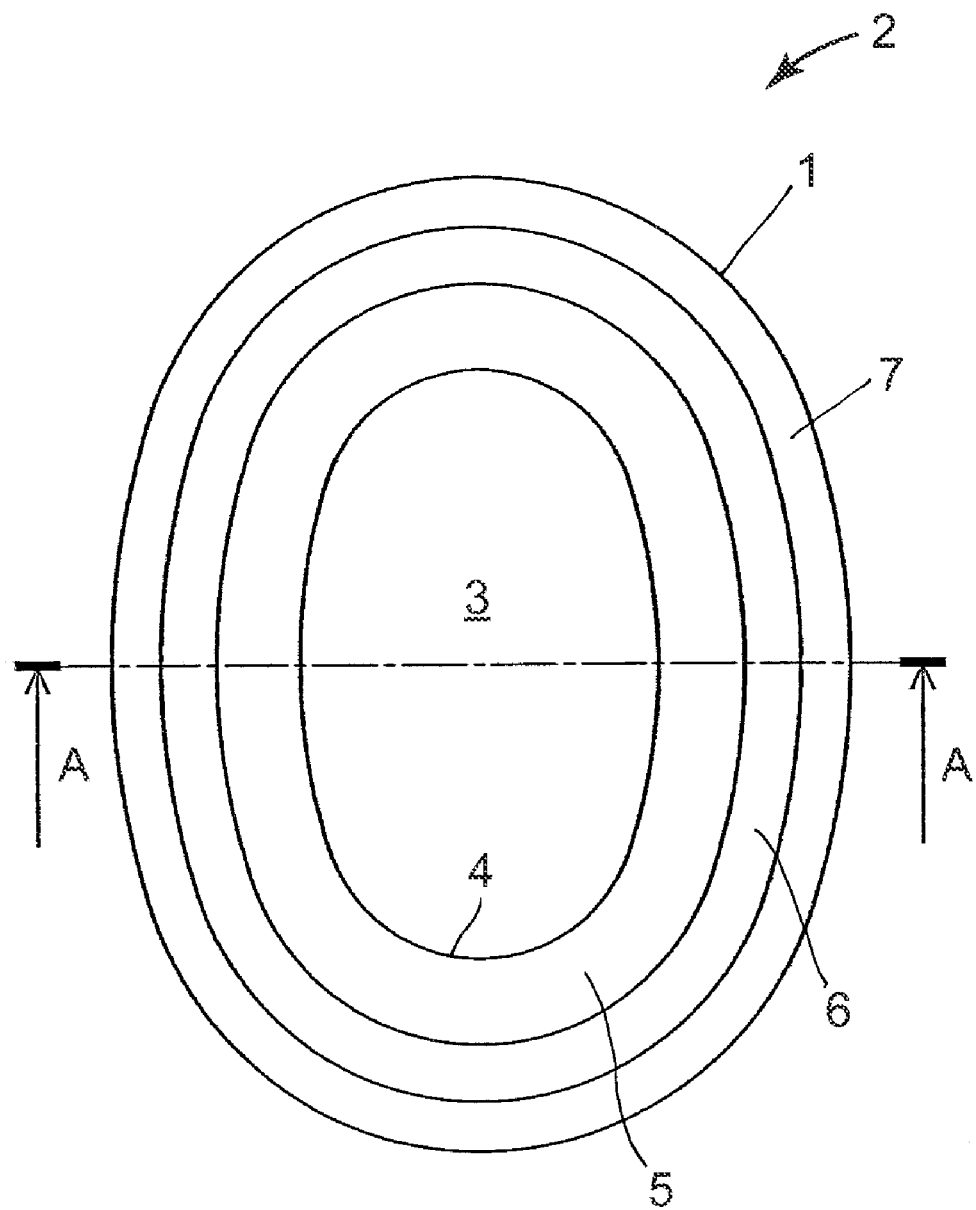
FIG. 1 is a plan view of a ear cup included in a hearing protector according to the present invention, seen from that direction which is turned to face towards the head of the wearer.

It will be apparent from FIG. 1 that the ear cups (not shown) included in the hearing protector according to the present invention display an oval outer contour 1. In actual fact, the outer contour 1 is also the outer contour of that sealing ring 2 which is secured along the periphery of the ear cups. The outer contour of the sealing ring is largely oval, but its detailed configuration may vary considerably from a substantially more circular shape to a considerably more flattened, elongate oval configuration. The sealing ring 2 has further, as is apparent from FIG. 1, a central region 3 which is defined by an inner contour 4 of the sealing ring 2. It will be apparent from the Figure that the distance between the outer contour 1 and the inner contour 4 is to all essentials the same 'all the way round'.

The sealing ring 2 comprises a number of circumferential lamellae disposed in a radial direction with interspacing outside one another, namely an inner lamella 5, an intermediate lamella 6 and an outer lamella 7. In this instance, the terms 'inner', 'intermediate' and 'outer' refer to the sequence in which the lamellae occur in direction from the central, inner region 3 of the sealing ring out to its outer contour 1.

In the embodiment under consideration here, as is apparent from the foregoing, the lamellae are three in number, but there are theoretical grounds that indicate that an increase of the number of lamellae would increase the sound damping capability of the sealing ring. At the same time, problems may be encountered in manufacture by injection molding. Even if three is the number to be preferred, as few as two may possibly be acceptable, but as large a number as may be handled in terms of production engineering affords further advantages. For practical reasons of production, the highest relevant number would probably lie in the range of between five and eight.

Figure 2:
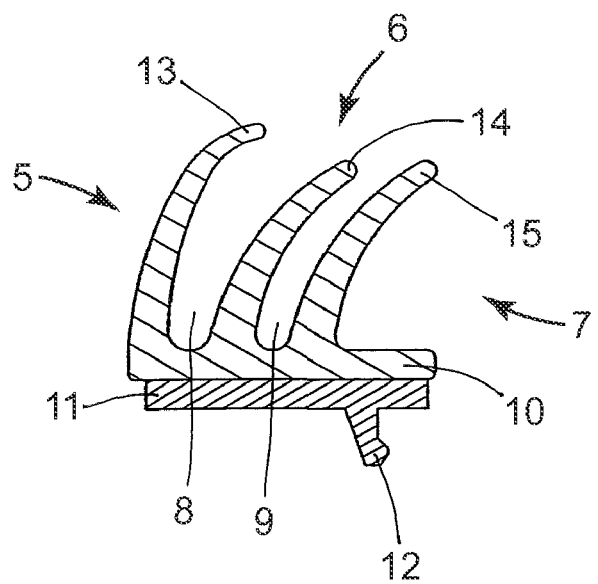
FIG. 2 is a section taken along the section line A-A in FIG. 1, only the sealing ring in the ear cup being shown.

It will be apparent from FIG. 2 that, between neighboring lamellae, there are gap-shaped circumferential spaces, an inner space 8 between the inner lamella 5 and the intermediate lamella 6, and an outer space 9 between the intermediate lamella 6 and the outer lamella 7. Both of these spaces 8 and 9 are of different widths in the radial direction, which implies that the resonance frequencies that may occur in the closed spaces thereby defined, when the lamellae abut against the wearer's skin, will be different. This contributes in the damping effect of the sealing ring 2.

It will further be apparent from FIG. 2 that the lamellae 5, 6 and 7 are mutually united by the intermediary of an annular base plate 10, which is substantially planar and, in the mounted state of the sealing ring on the ear cup, parallel with its free edge.

In the embodiment illustrated in FIG. 2, the base plate 10 of the sealing ring is secured or mounted on a mounting plate 11 which is also annular and substantially planar. The mounting plate 11 is manufactured from a configurationally stable material, preferably injection molded plastic material. Further, the mounting plate 11 displays, along a radial outer edge region, fixing means 12 for sealingly joining together with a corresponding fixing means, disposed along the peripheral region of the ear cup. The fixing means 12 is suitably designed as a snap device for accommodation in a corresponding undercut groove on the ear cup.

In the illustrated embodiment, the base plate 10 and the three lamellae 5, 6 and 7 are of one piece manufacture from the same material. In this embodiment, the base plate 10 is then connected, for example by gluing, to the mounting ring or plate 11.

According to the present invention, it however also possible to manufacture the mounting ring or plate 11 and the lamellae 5, 6 and 7 as a continuous material piece by 'double injection molding' with two different plastic materials in one injection molding tool. In such an embodiment, the base plate 10 may be more or less attenuated and possibly even completely dispensed with.

Figure 3:
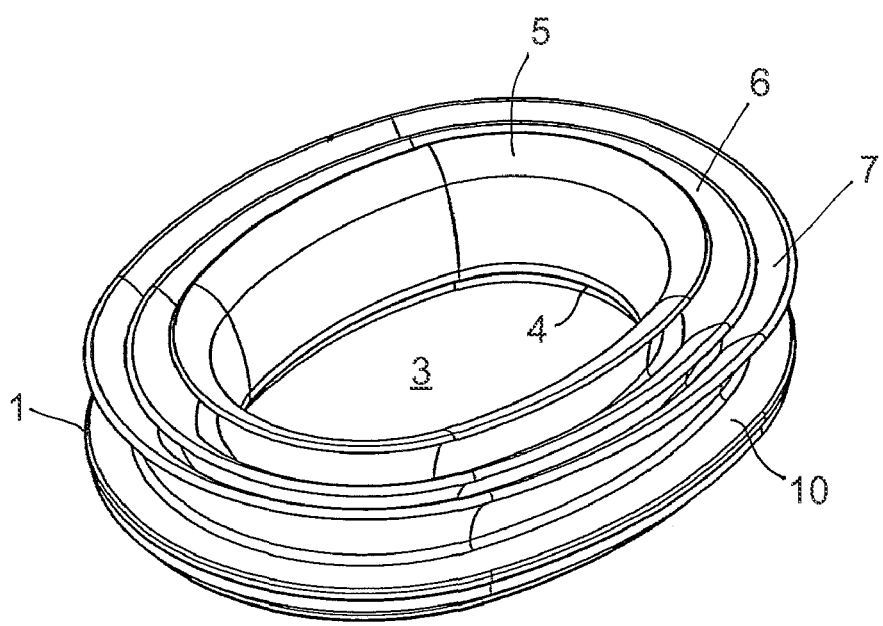
FIG. 3 is a perspective view of the sealing ring included in the hearing protector according to FIG. 1.

It will be apparent from FIGS. 2 and 3 taken together that the lamellae 5, 6 and 7 consist of funnel-shaped formations with their greatest cross-sectional dimension at their edge portions formed for abutment against the wearer's head. Generally viewed, the lamellae are obliquely directed from the central region of the sealing ring 2 out towards the periphery 1 in a direction away from the acoustic ear cup towards the wearer's head. It will further be apparent from FIG. 2 that the cross sections are gently arched and that the lamellae have outer edge portions 13, 14 and 15, respectively which are slightly more arched or curved radially outwards than is the case for the remaining portions of the lamellae. In practical, non-limiting embodiments the outer edge portions 13, 14 and 15 may have a radius of curvature of 5-10 mm, while the remaining portions of the lamellae have a radius of curvature of approximately 25-30 mm. These outer edge portions 13, 14 and 15 have slightly less material thickness than the remainder of the lamellae, which could have a thickness of approximately 2-5 mm, and are intended to be bent on contact against the head of the wearer so that band-shaped, relatively broad contact surfaces occur. As a result of the slightly reduced material thickness at the edge portions 13, 14 and 15, these portions will also be slightly more flexible than is the case for the remainder of the lamellae. Hereby, the ability of the lamellae to form and shape themselves in response to irregularities in the wearer's head is improved.

As a result of the slightly larger material cross sections and as a result of the direction of the portions of the lamellae located most proximal the base plate 10, there will be obtained an improved supporting effect from these portions of the lamellae.

It will be apparent from FIG. 2 that the radially innermost lamella 5 in the unloaded state, i.e. when the hearing protector is not being worn and, thus, is not pressed against the wearer's head, is of greater extent than the radially adjacent lamellae 6 and 7, lying radially outside in a direction away from the acoustic ear cup, i.e. from the base plate 10 and upwards in FIG. 2. In non-limiting embodiments, the height of the unloaded, innermost lamella 5 could be in the range of 15-20 mm, and the outermost lamella 1-3 mm shorter.

It will be apparent from the foregoing taken together regarding the spaces 8 and 9 that they have irregular configuration, with non-parallel defining surfaces. Such a configuration reduces the risk of 'standing waves' or other regular sound reverberations.

As was mentioned by way of introduction, the lamellae 5, 6 and 7 are produced from a resilient, possibly elastic material. This material is homogeneous and is thus not a foamed material with inner pores or the like. This implies that the defining surfaces of the lamellae, which also applies to the defining surfaces of the base plate 10, are smooth and substantially pore-free. Such a design of the defining surfaces entails that the sealing ring may readily be cleaned by washing.

A material which, regarding cleaning possibilities, is equivalent to a pore-free solid material is the so-called integral foam, i.e. a foamed material which has a dense surface skin without pores.

What is claimed is:

1. A hearing protector that comprises:
   two ear cups shaped to cover the ears of a wearer; and
   sealing rings that are secured along the peripheries of the ear cups, the sealing rings each displaying at least one circumferential lamella and comprising a resilient material to sealingly fit around the wearer's ears;
   wherein the lamella has edge regions configured to be located proximal the wearer's head, wherein the edge regions display portions that are arched in a direction toward the wearer from a central region in the sealing ring out towards its periphery.

2. The hearing protector of claim 1, wherein more than one lamella are disposed in a radial direction with spacing outside one another on each sealing ring.

3. The hearing protector of claim 2, wherein the lamellae constitute funnel-like formations, with their largest cross-sectional dimension at their edge portions formed for abutment against the wearer's head.

4. The hearing protector of claim 3, wherein the lamellae are mutually interconnected to one another by the intermediary of an annular base plate that is located on a side of the sealing ring facing towards the ear cup.

5. The hearing protector of claim 4, wherein the base plate is substantially planar.

6. The hearing protector of claim 4, wherein the base plate is substantially configurationally stable, and, along a radial outer edge region, the base plate is provided with fixing means for sealingly joining to the peripheral region of each ear cup.

7. The hearing protector of claim 4, wherein the base plate and the lamellae are formed in a single piece and the base plate is secured on a substantially configurationally stable mounting ring that, along a radial outer edge region, has fixing means for sealingly joining together with the peripheral region of each ear cup.

8. The hearing protector of claim 2, wherein neighboring lamellae define circumferential spaces, and wherein the spaces, are of different widths in the radial direction.

9. The hearing protector of claim 8, wherein the spaces are of irregular form, having non-parallel defining surfaces.

10. The hearing protector of claim 2, wherein the radially innermost lamella in an unloaded state has greater extension than radially adjacent lamellae in a direction away from the ear cup.

11. The hearing protector of claim 1, wherein the lamellae are of a material thickness that decreases in a direction away from each ear cup.

12. The hearing protector of claim 1, wherein the lamellae have defining surfaces that are smooth and substantially pore-free.

13. The hearing protector of claim 4, wherein the base plate has defining surfaces that are smooth and substantially pore-free.

* * * * *

UNITED STATES PATENT AND TRADEMARK OFFICE
CERTIFICATE OF CORRECTION

PATENT NO. : 8,302,731 B2  
APPLICATION NO. : 13/203253  
DATED : November 6, 2012  
INVENTOR(S) : Sigvard Nilsson Page 1 of 1

It is certified that error appears in the above-identified patent and that said Letters Patent is hereby corrected as shown below:

Title Page: Item 75

Line 1, delete "Vamamo (SE);" and insert -- Varnamo (SE); --, therefor.

Signed and Sealed this  
Twelfth Day of March, 2013

Teresa Stanek Rea  
*Acting Director of the United States Patent and Trademark Office*